United States Patent [19]

Ni et al.

[11] Patent Number: 5,786,153
[45] Date of Patent: Jul. 28, 1998

[54] PREVENTION OF PROBE COATING ON AUTOMATED ANALYZERS USING A NON-DENATURING SURFACTANT

[75] Inventors: Wei-Chao Ni, Foxborough; Anna Marie Detert, Quincy; James Joseph Hughes, Acton, all of Mass.

[73] Assignee: Chiron Diagnostics Corporation, East Walpole, Mass.

[21] Appl. No.: 712,829

[22] Filed: Sep. 12, 1996

[51] Int. Cl.$^6$ .................. G01N 33/53; G01N 35/02; A61K 35/14; C07K 16/00
[52] U.S. Cl. ................ 435/7.1; 435/7.5; 435/7.8; 435/7.92; 435/337; 530/380; 530/387.1; 436/500; 436/526; 436/544; 436/43
[58] Field of Search .................. 435/7.1, 7.4, 7.92, 435/7.8, 337, 287.2, 287.9, 7.93; 530/380, 387.1; 436/500, 526, 544, 8, 43, 47

[56] References Cited

U.S. PATENT DOCUMENTS

| | | | |
|---|---|---|---|
| 4,115,313 | 9/1978 | Lyon et al. | 250/309 |
| 5,066,336 | 11/1991 | Hoffman et al. | 134/22.12 |
| 5,395,545 | 3/1995 | Fischer et al. | 510/161 |
| 5,464,749 | 11/1995 | Schwarzberg et al. | 435/7.92 |
| 5,512,659 | 4/1996 | Ullman et al. | 530/391.1 |

FOREIGN PATENT DOCUMENTS

| | | |
|---|---|---|
| 0061541 A1 | 3/1981 | European Pat. Off. . |
| 669131 A1 | 8/1995 | European Pat. Off. . |
| 0743356 A1 | 5/1996 | European Pat. Off. . |

OTHER PUBLICATIONS

Campanella et al., Ann.Chim. 74(7–8); 483–497 (1984).
D'Alagni, M. et al., Colloid Polym. Sci. 263 (2); 160–163 (1985).

*Primary Examiner*—Ponnathapura Achutamurthy
*Assistant Examiner*—Padmashri Ponnaluri
*Attorney, Agent, or Firm*—Arthur S. Morgenstern; Helen Greer; Robert P. Blackburn

[57] ABSTRACT

A method for substantially preventing coating of hydrophobic material on a probe of an automated analyzer during an assay is described. An automated analyzer having a probe is provided. A composition comprising a non-denaturing surfactant and a reagent for use in the assay is provided. The probe is contacted with the composition during the assay such that hydrophobic material is substantially prevented from coating the probe on the automated analyzer. Compositions for preventing such probe coating are also described. Methods and compositions comprising a non-denaturing surfactant for enhancing the stability of reagents used in an assay are also described.

28 Claims, 2 Drawing Sheets

PREVENTION OF PROBE COATING ON AUTOMATED ANALYZERS USING A NON-DENATURING SURFACTANT

FIELD OF THE INVENTION

The present invention relates to methods and compositions or preventing coating of hydrophobic material on a probe of an automated analyzer during an assay.

BACKGROUND OF THE INVENTION

Certain assays which are performed using an automated analyzer often result in coating of the probe of the automated analyzer with hydrophobic material from assay reagents and/or products. Such probe coating can interfere with the accuracy of the assay results. It can result in crossover contamination from one type of assay to another if different assays are run sequentially. It can also result in inaccuracies for sequential assays of the same type, e.g., early assays in which the probe is either uncoated or partially coated, can give skewed results when compared to later-run similar assays which are run when the probe is completely coated. In addition, if a particular assay which results in probe coating is run in sequence in the middle of other types of assays in an automated analyzer, it can be difficult to compare the test data of the particular assay to any calibrated standard because of the uncertainty of the extent of probe coating.

One way that these problems have been addressed is to run multiple assays to pre-coat the probe before the actual test assays are run. Such a procedure, however, is highly impractical, particularly if a random access mode is being employed. Currently, performance of assays which result in probe coating have, therefore, generally been limited to the batch mode of analysis. Not having recourse to a random access mode severely limits the advantages of automated analyzers. For example, important assays which would ordinarily be part of a whole set of assays run together on a patient's blood sample, have to be separately and individually analyzed. This result is inefficient, time-consuming and costly.

SUMMARY OF THE INVENTION

It is an object of the invention to prevent coating of hydrophobic material on a probe of an automated analyzer during an assay.

It is another object of the invention to provide a safe, effective, easy and inexpensive method and composition for preventing coating of hydrophobic material on a probe of an automated analyzer.

It is yet another object of the invention to be able to accurately perform assays in either the batch mode or random access mode of an automated analyzer when the assay requires that the probe of the automated analyzer come into contact with a hydrophobic material.

It is yet another object of the invention to be able to obtain repeatable assay results starting with the first replicate through subsequent replicates, when using an automated analyzer in which the probe comes into contact with a hydrophobic material during the assay.

It is yet another object of the invention to prevent cross-contamination from one type of assay to another type of assay when multiple different assays are run in a random access mode of an automated analyzer and when the probe of the automated analyzer comes into contact with a hydrophobic material in one or more of the assays.

It is yet another object of the invention to eliminate the need for pre-coating the probe of an automated analyzer with a hydrophobic material before running test assays in which the probe will come into contact with that hydrophobic material.

It is yet another object of the invention to be able to run accurate assays for unsaturated thyroid binding proteins in serum or plasma using a random access mode on an automated analyzer.

Still another object of the invention is to enhance the stability of reagents used in certain assays.

According to the invention, a method for substantially preventing coating of hydrophobic material on a probe of an automated analyzer during an assay is provided. An automated analyzer having a probe is provided. A composition comprising a non-denaturing surfactant and a reagent for use in an assay is provided. The non-denaturing surfactant is capable of substantially preventing coating of the probe with hydrophobic material during the assay. The probe is contacted with the composition during the assay such that hydrophobic material is substantially prevented from coating the probe on the automated analyzer.

The non-denaturing surfactant can be, e.g., an anion surfactant, a zwitterion surfactant, a cation surfactant, or mixtures thereof. Preferably, the non-denaturing surfactant is sodium cholate or a sodium cholate analogue. In certain embodiments, the surfactant is, e.g., deoxycholic acid, glycocholic acid, lithocholic acid, taurocholic acid, CHAPS, CHAPSO, or their sodium salt derivatives.

In one embodiment, the assay is assessing unsaturated thyroid binding proteins in serum or plasma. The reagent can be, e.g., labeled triiodothyronine-BGG, unlabeled triiodothyronine, anti-triiodothyronine antibody coupled to magnetic particles, labeled thyroxine, unlabeled thyroxine, or anti-thyroxine antibody coupled to magnetic particles. The hydrophobic material can be, e.g., triiodothyronine or thyroxine.

Another aspect of the invention is a method for performing an assay using a random access mode of an automated analyzer. An automated analyzer having a probe and a random access mode is provided. A composition comprising a non-denaturing surfactant and a reagent for use in an assay is provided. The non-denaturing surfactant is capable of substantially preventing coating of the probe with hydrophobic material when performing the assay. The random access mode of the automated analyzer is used so as to perform the assay. In certain embodiments, the assay is the assessment of unsaturated thyroid binding proteins in serum or plasma.

Another aspect of the invention is a composition for use in substantially preventing coating of hydrophobic material on a probe of an automated analyzer during an assay. The composition comprises a non-denaturing surfactant and a reagent for use in the assay.

Another aspect of the invention is a method for enhancing the stability of a reagent used in assaying unsaturated thyroid binding proteins. A reagent for use in assaying unsaturated thyroid binding proteins is provided. A composition comprising a non-denaturing surfactant, e.g., an anion surfactant, a zwitterion surfactant or a cation surfactant, capable of enhancing the stability of the reagent is provided. The composition is contacted with the reagent such that the stability of the reagent is enhanced. Preferably, the non-denaturing surfactant is sodium cholate, a sodium cholate analogue, or mixtures thereof.

Another aspect of the invention is a composition for use in enhancing the stability of reagents used in assaying unsaturated thyroid binding proteins comprising a non-denaturing surfactant and a reagent for use in the assay.

The above and other objects, features and advantages of the present invention will be better understood from the following specification when read in conjunction with the accompanying drawings.

DETAILED DESCRIPTION

Figure 1:
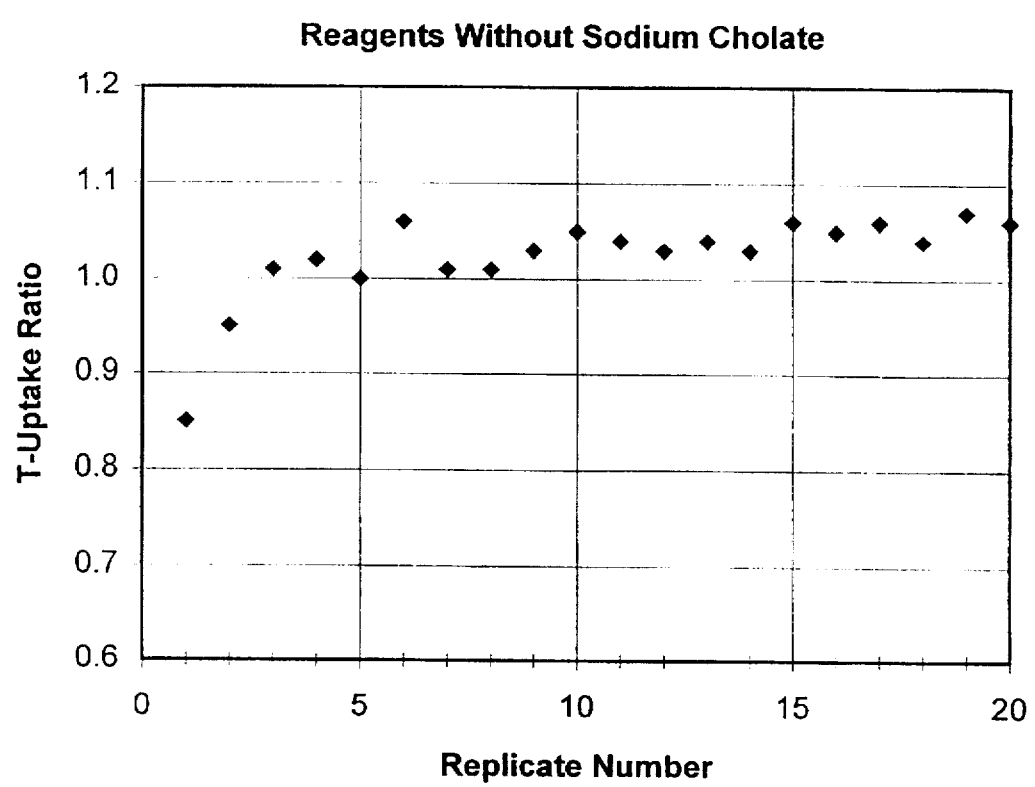
FIG. 1 depicts data for the T uptake ratio versus replicate number for assays assessing unsaturated thyroid binding proteins in serum performed using reagents without sodium cholate.

This invention provides a method for substantially preventing coating of hydrophobic material on a probe of an automated analyzer during an assay. An automated analyzer having a probe is provided. A composition comprising a non-denaturing surfactant and a reagent for use in an assay is provided. The non-denaturing surfactant is capable of substantially preventing coating of the probe with hydrophobic material during the assay. The probe is contacted with the composition during the assay such that hydrophobic material is substantially prevented from coating the probe on the automated analyzer.

By automated analyzer is meant an instrument system which combines reagents and samples in an automated fashion to produce test results. An example of an automated analyzer is the ACS:180 analyzer (Ciba-Corning, East Walpole, Mass.). By probe is meant a member of the automated analyzer which dispenses and/or mixes material, e.g., reagents, e.g., ligands, receptors, samples, cells, extracts, serum, plasma, labels, enzymes, antibodies, or any other material used for an assay that is to be performed by the automated analyzer. The automated analyzer functions by using any one or more modes for sample analysis, e.g., batch mode or random access mode. By batch mode is meant an operation on an automated analyzer which runs the same assay for a group of samples. By random access mode is meant an operation on an automated analyzer which runs multiple different assays for a group of samples. The running sequence of these different assays for a group of samples can be arranged in a random or non-random order.

The present invention is particularly useful for automated analyzers that utilize the random access mode. For example, prior to the present invention, in order to obtain more accurate test results, it would have been necessary to run multiple assays to pre-coat the probe before the actual test assay was run in order to prevent skewed data resulting from comparisons between use of uncoated, partially coated and fully coated probes. See, e.g., Example 1. Such a precoating procedure would be highly inefficient and impractical for certain types of assays in the random access mode, e.g., in tests in which only a single sample in a group of samples is to be tested using a particular assay. Thus, assays which give rise to probe coating were essentially limited to the batch mode in the prior art if accurate results were to be obtained. Since the present invention substantially prevents coating of the probe, a major advantage is that the assays can be accurately performed in either the batch mode or the random access mode.

The assay can be any assay which can be performed by an automated analyzer, e.g., immunoassays, enzymatic assays, chemical assays or biological assays. Preferably, the assay is one in which a material being dispensed or being formed is a hydrophobic material. By hydrophobic material is meant a material that dissolves poorly in water. Hydrophobic materials include, e.g., proteins, peptides, fats, oils and compounds such as triiodothyronine and thyroxine, and their analogues. Hydrophobic material accumulates on the probe of the automated analyzer because of the material's hydrophobic properties. This probe coating problem has generally limited such assays in the past to the batch mode only. Preventing coating of hydrophobic material on the probe during an assay is meant to include, e.g., before, during, or subsequent to the actual reaction step. For example, the invention includes preventing coating of the probe during probe dispension of an initial material, as well as preventing coating of the probe during probe dispension of a subsequent material. Prevention of probe coating during an assay is meant to include assays in which the probe comes into contact with either one or more materials, e.g., reagents, products, solutions, samples, or controls, either at the same time or sequentially.

Any assay in which coating of the probe by a material, e.g., a hydrophobic material, is a problem, can be performed using this invention. Such assays include, e.g., thyroxine (T4), triiodothyronine (T3), free thyroxine (free T4), free triiodothyronine (free T3), T uptake, or any other assay which uses hydrophobic molecules in the reagent formulation.

In a preferred embodiment of the invention, the assay is the assessment of unsaturated thyroid binding proteins in serum or plasma. Thyroid hormones, L-3,3',5-triiodothyronine ($T_3$) and thyroxine ($T_4$), are able to bind to thyroxine-binding globulin, thyroxine-binding prealbumin and albumin. The assay measures the number of unoccupied binding sites on these proteins in a sample, e.g., a serum sample, and is thus an indirect indicator of thyroid status. In a standard assay, the sample is incubated with a first reagent which comprises labeled $T_3$-bovine gamma globulin (BGG), e.g., acridinium ester (AE)-labeled $T_3$-BGG, and unlabeled $T_3$, preferably in phosphate buffer, EDTA and sodium azide. The unlabeled $T_3$ in the first reagent fills available thyroid binding sites in the sample. The AE-labeled $T_3$-BGG does not bind to the binding proteins in the sample. The AE-labeled $T_3$-BGG and unlabeled $T_3$ compete for anti-$T_3$ antibody, e.g., monoclonal mouse anti-$T_3$ antibody, present in a second reagent. Preferably, the second reagent comprises monoclonal mouse anti-$T_3$ antibody bound to goat anti-mouse antibody, which is coupled, e.g., covalently coupled, to magnetic, e.g., paramagnetic particles, preferably in phosphate buffer, EDTA and sodium azide. A greater amount of unlabeled $T_3$ binding to the binding proteins in the sample results in more AE-labeled $T_3$-BGG binding to the monoclonal antibody, an indication of a higher amount of unsaturated binding proteins. A direct relationship exists between the unsaturated binding proteins of a sample and the relative light units detected by an automated analyzer.

In certain embodiments, the assay for the assessment of unsaturated thyroid binding proteins in serum or plasma utilizes $T_4$ instead of $T_3$. For example, the first reagent comprises labeled $T_4$-BGG, e.g., AE-labeled $T_4$-BGG, and unlabeled $T_4$, and the second reagent comprises anti-$T_4$ antibody, e.g, monoclonal mouse anti-$T_4$ antibody bound to goat anti-mouse antibody, which is coupled, e.g., covalently coupled, to magnetic, e.g., paramagnetic particles. In these embodiments, the hydrophobic material is $T_4$, and the non-denaturing surfactant in the composition substantially prevents coating of the probe with $T_4$ during the assay.

By surfactant is meant a compound that reduces surface tension when dissolved in water, or which reduces interfacial tension between two liquids, or between a liquid and a solid, e.g., detergents, wetting agents or emulsifiers. An advantage of using a non-denaturing surfactant is that it will not denature the reagents and/or products with which it comes into contact. Examples of non-denaturing surfactants include anion surfactants, zwitterion surfactants, and cation surfactants. Preferably, the non-denaturing surfactant is sodium cholate or a sodium cholate analogue. Examples of non-denaturing surfactants that can be used in this invention include deoxycholic acid, glycocholic acid, lithocholic acid, taurocholic acid, CHAPS and CHAPSO, as well as the sodium salt derivatives of the above compounds. Any other surfactant which has a steroid backbone and sodium salt thereof, can also be used. A single non-denaturing surfactant can be used, or mixtures of non-denaturing surfactants can be used.

The concentration of the non-denaturing surfactant used is that concentration which is capable of substantially preventing coating of the probe with hydrophobic material during the assay. The optimum concentration may differ depending upon the specific non-denaturing surfactant that is used and the particular hydrophobic material that is present, and can be determined by one of ordinary skill in the art using no more than routine experimentation. Preferably, the concentration of the non-denaturing surfactant in the composition which also comprises a reagent for use in the assay is about 0.01% to about 10%, more preferably is about 0.05% to about 5%, and most preferably is about 0.1% to about 3%.

In certain embodiments in which multiple reagents are used in a particular assay, the non-denaturing surfactant can be added to either one or more of the different reagents to form different compositions. The concentrations of the non-denaturing surfactant can be the same or different in these various compositions with the different reagents. For example, in the embodiment discussed above in which the assay is the assessment of unsaturated thyroid binding proteins in serum or plasma, utilizing $T_3$, it is preferred that the concentrations of the surfactant, e.g., sodium cholate, contained in the first reagent and second reagent be different. The first reagent preferably contains about a 150-fold excess of unlabeled $T_3$ versus AE-labeled $T_3$-BGG based on molar ratio. The hydrophobic $T_3$ molecules are the cause of the coating problem on the probe. Preferably, the concentration of the surfactant in the first reagent is about 0.1% to about 3%, more preferably is about 0.1% to about 1%, and most preferably is about 0.2%. Standardly, the assay is performed by first pipetting the second reagent into the probe, followed by the first reagent. Subsequently, the first reagent is delivered into a reaction cuvette after the sample, followed by the second reagent. The part of the probe which has a $T_3$ coating problem is the portion that contains the first reagent, and not the portion that contains the second reagent. Therefore, a lower concentration of sodium cholate is preferred for the second reagent. Preferably, the concentration is such as to be able to scavenge any residual amount of $T_3$ left on the probe after delivery of the first reagent. Preferably, the concentration of the surfactant in the second reagent is about 0% to about 1%, more preferably about 0.01% to about 1%, more preferably yet about 0.02% to about 0.5%, and most preferably about 0.05%.

Depending upon the number and volumes of each composition that are used in a particular assay, the concentration of the non-denaturing surfactant in the actual reaction mixture may be reduced. For example, if two reagent compositions are added to a sample to form a reaction mixture, the concentration of the surfactant in the actual reaction mixture is calculated according to the following formula:(% surfactant in reagent I×reagent I volume)+(% surfactant in reagent II ×reagent II volume) divided by (sample volume+reagent I volume+reagent II volume).

Reagent is meant to include, e.g., any material which is needed for the assay, e.g., enzymes, antibodies, samples, cells, extracts, serum, plasma, labels, receptors, ligands, or any other chemical or biological moiety utilized as a reactant in the assay. Examples of reagents in the embodiments discussed above in which the assay is the assessment of unsaturated thyroid binding proteins in serum or plasma, are labeled $T_3$-BGG, unlabeled $T_3$, anti-$T_3$ antibody, labeled $T_4$-BGG, unlabeled $T_4$ and anti-$T_4$ antibody. The label can be, e.g. chemiluminescent, radioactive, enzymatic, latex agglutinant, bioluminescent, or fluorescent. A preferred label is acridinium ester.

The invention also includes a method for performing an assay using a random access mode of an automated analyzer. An automated analyzer having a probe and a random access mode is provided. A composition comprising a non-denaturing surfactant and a reagent for use in an assay is provided. The non-denaturing surfactant is capable of substantially preventing coating of the probe with hydrophobic material when performing the assay. The random access mode of the automated analyzer is used so as to perform the assay. In certain embodiments, the assay is the assessment of unsaturated thyroid binding proteins in serum or plasma.

The invention also includes a composition for use in substantially preventing coating of hydrophobic material on a probe of an automated analyzer during an assay. The composition comprises a non-denaturing surfactant and a reagent for use in the assay. The non-denaturing surfactant can be, e.g., an anion surfactant, a zwitterion surfactant, or mixtures thereof. Preferably, the non-denaturing surfactant is sodium cholate, a sodium cholate analogue, or mixtures thereof. In certain embodiments, the assay is the assessment of unsaturated thyroid binding proteins in serum or plasma. The reagent can be, e.g., labeled triiodothyronine-BGG, unlabeled triiodothyronine, anti- triiodothyronine antibody, labeled thyroxine, unlabeled thyroxine, and anti-thyroxine antibody.

In a preferred embodiment, the composition comprises sodium cholate and unlabeled triiodothyronine. In another preferred embodiment, the composition comprises sodium cholate and unlabeled thyroxine. In another preferred embodiment, the composition comprises sodium cholate and anti-triiodothyronine antibody. In another preferred embodiment, the composition comprises sodium cholate and anti-thyroxine antibody. In yet other preferred embodiments, a sodium cholate analogue is used instead of sodium cholate in each of the above-described compositions.

The invention also includes a method for enhancing the stability of a reagent used in assaying unsaturated thyroid binding proteins. A reagent for use in assaying unsaturated thyroid binding proteins is provided. A composition comprising a non-denaturing surfactant capable of enhancing the stability of the reagent is provided. The composition is contacted with the reagent such that the stability of the reagent is enhanced.

A reagent for assaying unsaturated thyroid binding proteins includes, e.g., reagents comprising labeled triiodothyronine-BGG and unlabeled triiodothyronine, or anti-triiodothyronine antibody coupled to magnetic particles, or labeled thyroxine and unlabeled thyroxine, or anti-thyroxine antibody coupled to magnetic particles. The invention is also meant to cover any other reagent formulation that is used in assaying unsaturated thyroid binding proteins.

By enhancing the stability of a reagent is meant increasing the retention of activity of the reagent when the reagent is aged. The activity of the reagent is usually reflected in signals, such as chemiluminescence, fluorescence or radioactivity. In certain embodiments, the stored calibration stability is enhanced; in other embodiments, the on-board stability of the reagent is enhanced; in yet other embodiments, both the stored calibration and the on-board stabilities are enhanced. By stored calibration stability is meant the extent of deviation of control dose recovery from 100% as a reagent is aged under the specified storage condition. The dose recovery is measured from the time 0 stored calibration point and compared with the control dose recovery at time 0. By on-board stability is meant the extent of deviation of the control dose recovery from 100% as a reagent is placed on the instrument under the running conditions for a prolonged time. The dose recovery is measured from the time 0 stored calibration point and compared with the control dose recovery at time 0.

The non-denaturing surfactant can be, e.g., an anion surfactant, a zwitterion surfactant, a cation surfactant, or mixtures thereof. Preferred non-denaturing surfactants are sodium cholate, a sodium cholate analogue, or mixtures thereof. The concentration of the non-denaturing surfactant will vary depending upon the specific reagent used and the specific non-denaturing surfactant used, and can be determined by one skilled in the art using no more than routine experimentation. Preferably, the concentration of the surfactant in the reagent is about 0.01% to about 3%, more preferably is about 0.02% to about 1%, and most preferably is about 0.05% to about 0.2%.

The invention also includes a composition for use in enhancing the stability of reagents used in assaying unsaturated thyroid binding proteins comprising a non-denaturing surfactant and a reagent for use in the assay. The non-denaturing surfactant can be, e.g., an anion surfactant, a zwitterion surfactant, a cation surfactant, or mixtures thereof. Preferred non-denaturing surfactants are sodium cholate, a sodium cholate analogue, or mixtures thereof.

The following non-limiting examples further illustrate the present invention.

EXAMPLES

Example 1

Comparison Studies of Uptake Ratios of Thyroid Binding Proteins Using Reagents With and Without Sodium Cholate This example illustrates that the addition of sodium cholate to the reagents in repeated assays for assessing unsaturated thyroid binding proteins resulted in about 0% difference between the first and subsequent replicates, as compared to using reagents without sodium cholate which resulted in about a 19% difference between the first and subsequent replicates.

Figure 2:
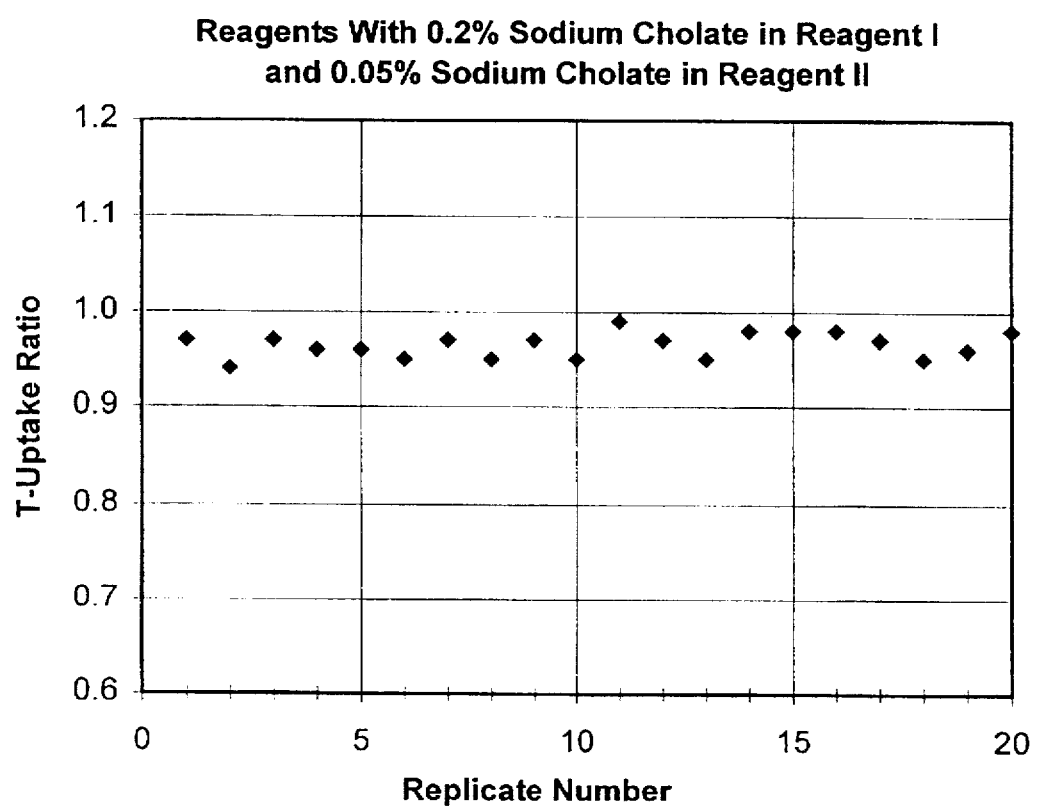
FIG. 2 depicts data for the T uptake ratio versus replicate number for assays assessing unsaturated thyroid binding proteins in serum performed using reagents with sodium cholate.

The assays were performed as follows, using an ACS:180 analyzer and Reagent Probe 2 (Ciba-Corning, East Walpole, Mass.): 35 µl of serum sample was dispensed into a cuvette; 100 µl of reagent I (AE-labeled $T_3$-BGG, unlabeled $T_3$, phosphate buffer, EDTA and sodium azide (0.1%), was then dispensed; 450 µl of reagent II (monoclonal mouse anti-$T_3$ antibody bound to goat anti-mouse antibody covalently coupled to paramagnetic particles, phosphate buffer, EDTA and sodium azide (0.1%)), was then dispensed; the mixture was incubated for 5 minutes at 37° C.; the cuvette was separated, aspirated and washed with deionized water; 300 µl of an acid reagent (a mixture of 0.1N nitric acid and 0.5% hydrogen peroxide) and 300 µl of a base reagent (a mixture of 0.25N sodium hydroxide and 0.15% Arqad) was then dispensed to initiate the chemiluminescent reaction; the results were obtained on the automated analyzer. The above reagents for this assay can be obtained from Ciba-Corning, East Walpole, Mass. (ACS:180 TUptake Assay Package). The assays were performed either with no addition of sodium cholate, or with sodium cholate (0.2% final concentration) added to reagent I, and sodium cholate (0.05% final concentration) added to reagent II. The addition of sodium cholate to the reagents eliminated the probe coating problem completely. See FIG. 1 (experiments performed without sodium cholate) and FIG. 2 (experiments performed with sodium cholate). The percent difference in T uptake ratios between the first replicate and the mean of replicates from the thirteenth to the twentieth was 19.0 for the reagents without sodium cholate and 0 for the reagents with sodium cholate. The percent difference was calculated as [(mean of replicates 13 through 20)−(first replicate)]×(100) divided by (mean of replicates 13 through 20).

Example 2

Addition of Sodium Cholate in Thyroid Protein Binding Assays Results in the Absence of $T_3$ in Washes of the Probes This example illustrates that assays for assessing unsaturated thyroid binding proteins performed with sodium cholate present in the reagents gave rise to probes which when washed showed no detectable levels of L-3,3',5-triiodothyronine ($T_3$).

The assays were performed with and without sodium cholate as described in Example 1. The assays were run fifty times each on two different ACS:180 analyzers. At the end of the run, the probes on the analyzers were washed and soaked in 3 ml methanol. The methanol wash was analyzed and showed that about 10 ng/ml of $T_3$ was contained in the wash from the assays without the sodium cholate and was not detectable from the assays with sodium cholate.

Example 3

Addition of Sodium Cholate in Thyroid Protein Binding Assays Does Not Interfere With Other Assays Using a Random Access Mode This example illustrates that the use of sodium cholate in assays for assessing unsaturated thyroid binding proteins using a random access mode on an automated analyzer did not interfere with other types of assays performed in the random access mode.

The assay for assessing unsaturated thyroid binding proteins was performed as described in Example 1, using reagents which contained 0.2% sodium cholate in reagent I and 0.05% sodium cholate in reagent II. This assay was tested in a random access mode on an ACS:180 analyzer with other probe 2 assays: cortisol, testosterone, progesterone, folate 2, estradiol-6 and TSH 3 assays. See Ciba Corning (Medfield, Mass.) ACS:180 package inserts for these assays as in use for the year 1996. The results showed that the presence of sodium cholate in the thyroid binding protein assay did not interfere with any of the other assays tested, and that none of these other assays interfered with the thyroid binding protein assay.

Example 4

Comparison Studies of Uptake Ratios of Thyroid Binding Proteins Using Reagents With and Without Various Non-Denaturing Surfactants This example illustrates that sodium cholate analogue surfactants resulted in substantially preventing probe coating when added to the reagents in assays for assessing unsaturated thyroid binding proteins.

The assays were performed as described in Example 1, except that a variety of sodium cholate analogues were added to the reagents instead of sodium cholate. The analogues used were: sodium salt of deoxycholic acid, sodium salt of glycocholic acid, lithocholic acid, sodium salt of taurocholic acid, CHAPS and CHAPSO. The concentration of the surfactant in reagent I and reagent II was 0.5%. The comparison study results among the various analogues are shown in Table 1.

TABLE 1

Prevention of Probe Coating in Thyroid Binding Protein Assays: Effect of Non-Denaturing Surfactants

| Reagents With 0.5% Surfactant in Reagent I and II | T Uptake Ratio First Replicate | T Uptake Ratio Mean of Replicates (13–20) | Percent Difference |
|---|---|---|---|
| No surfactant | 0.87 | 1.11 | 21.6 |
| Cholic acid, sodium salt | 0.97 | 1.00 | 3.0 |
| Cholic acid | 1.06 | 1.15 | 8.0 |
| Deoxycholic acid, sodium salt | 1.18 | 1.14 | −3.3 |
| Glycocholic acid, sodium salt | 0.96 | 1.00 | 4.4 |
| Lithocholic acid | 0.96 | 1.07 | 10.0 |
| Taurocholic acid, sodium salt | 1.05 | 1.04 | −0.6 |
| CHAPS | 0.97 | 1.11 | 12.8 |
| CHAPSO | 0.94 | 1.00 | 6.1 |

In comparing the percent difference in T uptake ratios between the first replicate and the mean of replicates from the thirteenth to the twentieth, the largest difference, 21.6%, was obtained from the reagents which did not contain any surfactant. All of the surfactants reduced the extent of $T_3$ probe coating compared with that of the no surfactant condition.

Example 5

Comparison Studies of Reagent Stability With and Without Sodium Cholate

This example illustrates that the addition of sodium cholate to reagents used in assays for assessing unsaturated thyroid binding proteins enhanced the stability of the reagents.

(a) Stored Calibration Stability

At day 0, a calibration point from the reagent formulations I and II (described in Example 1) was stored on an ACS:180 analyzer. A time-course study using the stored calibration point was followed subsequently for 28 days. The reagents were stored at 2°–8° C. in a separate refrigerator.

On a specific day, uptake ratios of thyroid binding proteins using reagents with and without sodium cholate, as described in Example 1, were performed. Each data point was calibrated from the day 0 stored calibration point for the corresponding reagent stored at 2°–8° C. The percent of dose recoveries of controls and patient sample pools with respect to day 0 was determined. Higher deviation from 100% recoveries was observed in the reagent formulations without sodium cholate, whereas closer to 100% recoveries were observed in the reagent formulations with sodium cholate. Statistical analysis of the recoveries confirmed that there as a significant difference overall for the stored calibration stability between the reagent formulations with and without sodium cholate over 28 days. Thus, the reagents with sodium cholate rendered better stability than those without sodium cholate.

In sum, the stored calibration stability data showed that sodium cholate slows down the gradual loss of signal (chemiluminescence) when the reagents were stored at 2°–8° C.

(b) On-Board Stability

The reagents as described in (a) were continuously stressed in a stability chamber (Webber Manufacturing Co., Inc., Indianapolis, Ind.) at 30° C. and 20% relative humidity for 48 hours. ACS:180 reagent wheels were placed inside of the stability chamber. The reagent II bottles were constantly rotated on the reagent wheel to prevent the settling of paramagnetic particles. Both reagent I and reagent II bottles were partially open on the reagent wheel inside the stability chamber throughout the entire study. These conditions were designated to simulate the ACS:180 instrument running conditions. At a specific time point, an aliquot of the reagent was removed and discarded to simulate actual usage; the remaining reagent bottles were retired to storage at 2°–8° C. The retired reagents were tested and analyzed based on a stored calibration from the time 0 reagents. The percent of control recoveries with respect to that of time 0 were determined. Lower percent recoveries were observed in the reagent formulations without sodium cholate, whereas near 100% recoveries were observed in the reagent formulations with sodium cholate. Statistical analysis of the recoveries confirmed that there was a significant difference for the on-board stability over 48 hours between the reagent formulations with and without sodium cholate. Thus, the addition of sodium cholate improved the on-board stability of the reagents in the unsaturated thyroid binding protein assay.

Those skilled in the art will be able to ascertain, using no more than routine experimentation, many equivalents of the specific embodiments of the invention described herein. These and all other equivalents are intended to be encompassed by the following claims.

What is claimed is:

1. A method for preventing or reducing coating of hydrophobic material on a probe of an automated analyzer during an assay, comprising:

providing an automated analyzer having a probe;

providing a composition comprising a non-denaturing surfactant and a reagent for use in an assay, said non-denaturing surfactant being capable of preventing or reducing coating of said probe with hydrophobic material during the assay; and contacting said probe with said composition during the assay such that hydrophobic material is prevented or reduced from coating said probe on said automated analyzer.

2. The method of claim 1 wherein said non-denaturing surfactant is an anion surfactant.

3. The method of claim 1 wherein said non-denaturing surfactant is a zwitterion surfactant.

4. The method of claim 1 wherein said non-denaturing surfactant is a cation surfactant.

5. The method of claim 1 wherein said non-denaturing surfactant is sodium cholate.

6. The method of claim 1 wherein said non-denaturing surfactant is a sodium cholate analogue.

7. The method of claim 1 wherein said non-denaturing surfactant is selected from the group consisting of deoxycholic acid, glycocholic acid, lithocholic acid, taurocholic acid, CHAPS, CHAPSO, their sodium salt derivatives, and mixtures thereof.

8. The method of claim 1 wherein the concentration of said non-denaturing surfactant in said composition is about 0.01% to about 10%.

9. The method of claim 1 wherein the concentration of said non-denaturing surfactant in said composition is about 0.1% to about 3%.

10. The method of claim 1 wherein the concentration of said non-denaturing surfactant in said composition is about 0.01% to about 1%.

11. The method of claim 1 wherein said reagent is for assaying unsaturated thyroid binding proteins in serum or plasma.

12. The method of claim 11 wherein said reagent comprises labeled triiodothyronine-bovine gamma globulin and unlabeled triiodothyronine.

13. The method of claim 11 wherein said reagent comprises anti-triiodothyronine antibody coupled to magnetic particles.

14. The method of claim 11 wherein said reagent comprises labeled thyroxine-bovine gamma globulin and unlabeled thyroxine.

15. The method of claim 11 wherein said reagent comprises anti-thyroxine antibody coupled to magnetic particles.

16. The method of claim 11 wherein said hydrophobic material is triiodothyronine.

17. The method of claim 11 wherein said hydrophobic material is thyroxine.

18. A method for performing an assay using a random access mode of an automated analyzer, comprising:

providing an automated analyzer having a probe and a random access mode;

providing a composition comprising a non-denaturing surfactant and a reagent for use in an assay, said non-denaturing surfactant being capable of preventing or reducing coating of said probe with hydrophobic material when performing the assay; and using the random access mode of said automated analyzer so as to perform the assay.

19. The method of claim 18 wherein the assay is the assessment of unsaturated thyroid binding proteins in serum or plasma.

20. A method for enhancing the stability of a reagent used in assaying unsaturated thyroid binding proteins, comprising:

providing a reagent selected from the group consisting of labeled triiodothyronine-bovine gamma globulin, unlabeled triiodothyronine, anti-triiodothyronine antibody coupled to magnetic particles, labeled thyroxine-bovine globulin and unlabeled throxine and anti-thyroxine antibody coupled to magnetic particles, for use in assaying unsaturated thyroid binding proteins;

providing a composition comprising a non-denaturing surfactant capable of enhancing the stability of said reagent; and contacting said composition with said reagent such that the stability of said reagent is enhanced.

21. The method of claim 20 wherein said reagent comprises labeled triiodothyronine-bovine gamma globulin and unlabeled triiodothyronine.

22. The method of claim 20 wherein said reagent comprises anti-triiodothyronine antibody coupled to magnetic particles.

23. The method of claim 20 wherein said reagent comprises labeled thyroxine-bovine gamma globulin and unlabeled thyroxine.

24. The method of claim 20 wherein said reagent comprises anti-thyroxine antibody coupled to magnetic particles.

25. The method of claim 20 wherein said non-denaturing surfactant is selected from the group consisting of an anion surfactant, a zwitterion surfactant, a cation surfactant, and mixtures thereof.

26. The method of claim 20 wherein said non-denaturing surfactant is selected from the group consisting of sodium cholate, a sodium cholate analogue, and mixtures thereof.

27. The method of claim 20 wherein the on-board stability of said reagent is enhanced.

28. The method of claim 20 wherein the stored calibration stability of said reagent is enhanced.

* * * * *